United States Patent [19]

Gutierrez et al.

[11] Patent Number: 5,195,197
[45] Date of Patent: Mar. 23, 1993

[54] MATTRESS LINER WITH MAGNETS IN POCKETS

[76] Inventors: Hector Gutierrez; Yamile Gutierrez, both of P.O. Box 451804, Miami, Fla. 33245

[21] Appl. No.: 952,592
[22] Filed: Sep. 28, 1992
[51] Int. Cl.⁵ .......................... A47G 9/00; A47G 9/04
[52] U.S. Cl. ........................................ 5/500; 5/482; 5/485; 5/906
[58] Field of Search ................... 5/500, 502, 499, 485, 5/482, 906, 496

[56] References Cited

U.S. PATENT DOCUMENTS

| | | | |
|---|---|---|---|
| 2,596,547 | 5/1952 | Guest | 5/485 |
| 4,330,892 | 5/1982 | Fukushima | 5/906 |
| 4,509,219 | 4/1985 | Yagi | 5/906 |

FOREIGN PATENT DOCUMENTS

| | | | |
|---|---|---|---|
| 0356594 | 3/1990 | European Pat. Off. | 5/482 |
| 3522667 | 1/1987 | Fed. Rep. of Germany | 5/482 |
| 8401517 | 4/1984 | PCT Int'l Appl. | 5/482 |
| 13980 | 6/1896 | United Kingdom | 5/485 |
| 2198348 | 6/1988 | United Kingdom | 5/485 |

Primary Examiner—Alexander Grosz
Attorney, Agent, or Firm—Malloy, Downey & Malloy

[57] ABSTRACT

A mattress liner to substantially cover a mattress surface, the mattress liner including a mattress pad having a top surface and a bottom surface, and a plurality of substantially thin magnets releasably disposed in pockets substantially spaced apart relation from one another along the bottom surface of the mattress pad and secured thereto.

8 Claims, 1 Drawing Sheet

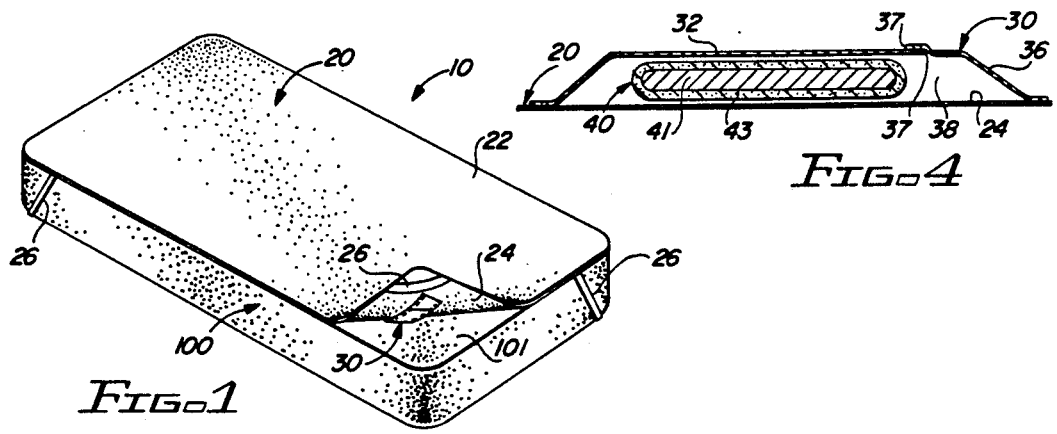
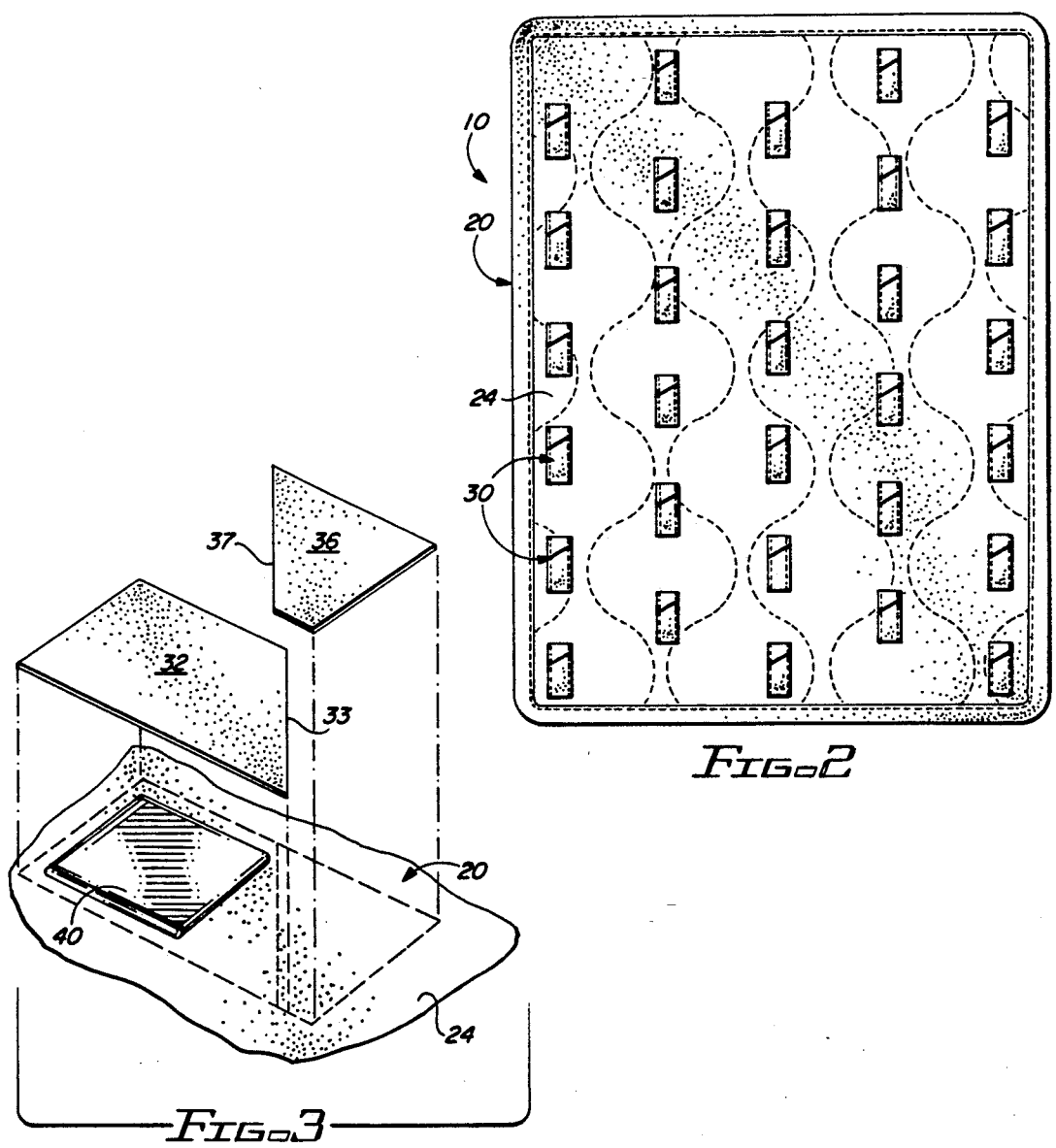

MATTRESS LINER WITH MAGNETS IN POCKETS

FIELD OF THE INVENTION

This invention relates to a mattress liner, and more particularly, to what is known as a mattress pad.

BACKGROUND OF THE INVENTION

In the past, there have been numerous types of mattress liners adapted to overly a mattress surface and substantially cover it. Conventionally, this has included a mattress pad secured about its periphery to the mattress surface and adapted to provide a covering and padding layer.

SUMMARY OF THE INVENTION

The present invention is directed towards an improved mattress liner of the type designed to be disposed over a mattress surface in substantially covering relation thereto. It includes primarily a mattress pad having a top surface and a bottom surface, the mattress pad being sized to a particular size mattress surface such that it may completely overly it. Additionally, the mattress liner includes a plurality of substantially thin magnets. The magnets are secured to the bottom surface of the mattress pad in substantially spaced apart relation from one another. Accordingly, the magnets are evenly distributed along substantially the entire bottom surface of the mattress pad.

It is an object of the present invention to provide a mattress liner, having a plurality of substantially thin magnets therein, adapted to be disposed in substantially covering relation over a mattress surface, yet be substantially comfortable such that an individual using the mattress will not experience discomfort as a result of the magnets.

Yet another object of the present invention is to provide a mattress liner including a plurality of substantially thin magnets therein, the magnets being substantially secured to a mattress pad and being well-contained so as to remain properly positioned and be free from corrosion or oxidation.

Still another object of the present invention is to provide a mattress liner which will comfortably provide an evenly distributed magnetic field along a mattress surface.

BRIEF DESCRIPTION OF THE DRAWINGS

For a fuller understanding of the nature of the present invention, reference should be had to the following detailed description taken in combination with the accompanying drawings in which:

FIG. 1 is an elevated perspective view of the mattress liner in use atop a mattress.

FIG. 2 is a bottom view of the mattress liner of the present invention.

FIG. 3 is an exploded view of a pocket on the mattress liner of the present invention.

FIG. 4 is a cross-sectional view of the pocket of the mattress liner of the present invention.

Like reference numerals refer to like parts throughout the several views of the drawings.

DETAILED DESCRIPTION OF THE PREFERRED EMBODIMENT

Shown throughout FIGS. 1-4, the present invention is directed towards a mattress liner, generally indicated as 10. The mattress liner 10 is primarily adapted to be used atop a mattress 100, and may be sized and configured such that it completely overlies an entire mattress surface 101. Further, the mattress liner 10 can be effectively disposed on either the top or the bottom mattress surface 101.

Referring to FIGS. 1 and 2, the mattress liner 10 includes primarily a mattress pad 20. The mattress pad 20, which may be of cotton or a like soft padded material includes a top surface 22 and a bottom surface 24. When in use on a mattress 100, the mattress pad 20 may be secured by a plurality of straps 26, or any other like conventionally-known securing means, such as pins, ties, or an elastic skirt however, as in the embodiment shown in FIG. 2, no fastening means are required to effectively utilize the mattress pad 20.

Disposed along the bottom surface 24 of the mattress pad 20 are a plurality of pockets 30. The pockets 30 are evenly distributed along the bottom surface 24 of the mattress pad 20, in substantially spaced apart relation from one another, and as shown in FIG. 2, may be ordered in a plurality of evenly spaced rows. Contained within each of the pockets 30 is a thin magnet 40, and as a result of the spaced arrangement of the pockets 30, the magnets 40 are secured to the mattress pad 20 in the spaced apart array, thereby providing an evenly distributed magnetic field along the entire mattress surface 101.

Turning to FIGS. 3 and each of the pockets 30 includes a material layer 32 which is generally larger than the magnet 40 so as to completely overlay it. The material layer 32 is stitched to the bottom surface 24 of the mattress pad 20 along three of four outer edges thereof, thereby leaving only a top outer edge 33 unstitched. Accordingly, an interior holding cavity 38 is formed between the material layer 32 and the bottom surface 24 of the mattress pad 20 wherein the magnet 40 may be securely contained and accessed solely through the top unstitched outer edge 33. In order to securely maintain the magnet 40 within the holding cavity 38, the pocket 30 includes a cover flap 36 adapted to overly the material layer 32 and prevent unwanted passage of the magnet 40 from the holding cavity 38. In the preferred embodiment, the cover flap 38 is stitched to the bottom surface 24 of the mattress pad 20 in a position directly above the material layer 30. The cover flap 36 is similarly stitched along three of four peripheral edges thereof, leaving only a bottom peripheral edge 37 unstitched. The bottom peripheral edge 37 is disposed in overlapping position over the unstitched top outer edge 33 of the material layer 32 such that access to the interior hollow cavity 38 may be solely achieved therebetween. As a result of the overlying configuration, the magnet 40 will remain secure within the interior holding cavity 38 despite any sliding or movement within the interior holding cavity 38.

Each of the magnets 4 is substantially thin such that they are not uncomfortable to an individual lying atop the mattress liner 10. Additionally, since the magnets 40 will remain contained within the pockets 30 for substantial periods of time, each of the magnets 40 includes an outer plastic coating 43 which contains the magnetic plate 41. The outer plastic coating 43 is adapted such that the magnetic properties of the magnetic plate 41 are not hindered yet corrosion or oxidation of the magnetic plate 41 will not result after prolonged use. Therefore, the mattress liner 10 may be used for extended periods of time to provide a magnetic field over the mattress surface 101.

Now that the invention has been described,
What is claimed is:

1. A mattress liner comprising:
a mattress pad, said pad including a top surface and a bottom surface, and being structured and disposed to substantially cover a mattress surface,
a plurality of substantially thin magnets, and
means to releasably secure said magnets to said bottom surface of said mattress pad in substantially spaced apart relation from one another, said means including a plurality of pockets disposed in spaced apart relation from one another along said bottom surface of said mattress pad, each of said pockets being structured and disposed to removably contain one of said magnets securely therein, said pockets including an outer material layer having outer edges, said material layer being stitched to said bottom surface of said mattress pad about a portion of the periphery thereof along said outer edges so as to form an interior holding cavity between said bottom surface of said mattress pad and said material layer, said holding cavity being structured and disposed to contain one of said magnets therein.

2. A mattress liner as recited in claim 1 wherein each of said magnets is encased in plastic.

3. A mattress liner as recited in claim 4 wherein each of said pockets includes a cover flap including four peripheral edges, said cover flap being structured and disposed to overly said material layer.

4. A mattress liner as recited in claim 3 wherein said cover flap is stitched to said bottom surface of said mattress pad along three of said four peripheral edges thereof and is structured and disposed such that a bottom, unstitched peripheral edge thereof is disposed in overlapping position atop a top unstitched outer edge of said material layer, thereby enabling said interior holding cavity to be accessible therebetween.

5. A mattress liner as recited in claim 4 wherein said plurality of magnets are disposed in a plurality of even rows along said bottom surface of said mattress pad.

6. A mattress liner as recited in claim 4 wherein said mattress pad includes fastening means structured and disposed to maintain said mattress in overlying position on said mattress surface.

7. A mattress liner as recited in claim 6 wherein said mattress pad is disposed on a bottom surface of the mattress.

8. A mattress liner as recited in claim 6 wherein said mattress pad is disposed on a top surface of the mattress.

* * * * *